United States Patent
He et al.

(10) Patent No.: US 12,171,459 B2
(45) Date of Patent: Dec. 24, 2024

(54) AUXILLIARY DEVICE AND AUXILLIARY METHOD FOR EPIDURAL ANESTHESIA NEEDLE PLACEMENT

(71) Applicant: HANGZHOU SANTAN MEDICAL TECHNOLOGY CO., LTD, Zhejiang (CN)

(72) Inventors: Bin He, Zhejiang (CN); Liping Shen, Zhejiang (CN); Rui Tong, Zhejiang (CN); Hanqing Chen, Zhejiang (CN)

(73) Assignee: HANGZHOU SANTAN MEDICAL TECHNOLOGY CO., LTD, Hangzhou (CN)

( * ) Notice: Subject to any disclaimer, the term of this patent is extended or adjusted under 35 U.S.C. 154(b) by 364 days.

(21) Appl. No.: 17/869,986

(22) Filed: Jul. 21, 2022

(65) Prior Publication Data
US 2022/0354534 A1    Nov. 10, 2022

Related U.S. Application Data

(63) Continuation of application No. PCT/CN2021/075507, filed on Feb. 5, 2021.

(30) Foreign Application Priority Data

Feb. 17, 2020   (CN) .......................... 202010096939.8
Feb. 17, 2020   (CN) .......................... 202010096955.7

(51) Int. Cl.
*A61M 5/20*      (2006.01)
*A61B 5/05*      (2021.01)
(Continued)

(52) U.S. Cl.
CPC .............. *A61B 17/34* (2013.01); *A61B 34/10* (2016.02); *A61B 34/20* (2016.02); *A61B 17/3403* (2013.01)

(58) Field of Classification Search
USPC ................ 128/897–899, 912, 620, 922–925; 382/311–325, 151–155, 128; 604/48,
(Continued)

(56) References Cited

U.S. PATENT DOCUMENTS

| | | |
|---|---|---|
| 4,414,983 A | 11/1983 | Evans et al. |
| 5,104,382 A | 4/1992 | Brinkerhoff et al. |

(Continued)

FOREIGN PATENT DOCUMENTS

| | | |
|---|---|---|
| CN | 102083377 A | 6/2011 |
| CN | 105963018 A | 9/2016 |

(Continued)

*Primary Examiner* — Marcellus J Augustin

(57) ABSTRACT

The present disclosure relates to an auxiliary device and auxiliary method for epidural anesthesia needle placement, the auxiliary device comprising: a needle placement unit (1), a motion guide unit (2) for driving the needle placement unit into movement, and a control unit (3) for supporting and controlling the motion guide unit (2), the needle placement unit (1) being electrically connected to the control unit (3); the needle placement unit (1) comprises: a first support (11) connected to the motion guide unit (2), a second support (12) slidably connected with the first support (11), a needle placement assembly (13) slidably connected with the second support (12), and a first drive (14) arranged on the first support (11) for driving the second support (12) into motion. The scheme of the present disclosure may perform a real-time multidimensional monitoring to the puncture process, achieving autonomous, precise, safe needle placement and puncture operations.

12 Claims, 5 Drawing Sheets

(51) Int. Cl.
*A61B 17/34* (2006.01)
*A61B 34/10* (2016.01)
*A61B 34/20* (2016.01)

(58) Field of Classification Search
USPC .................................................. 604/500–512
See application file for complete search history.

(56) References Cited

U.S. PATENT DOCUMENTS

| | | | |
|---|---|---|---|
| 8,715,234 B2* | 5/2014 | Bethi | A61B 17/3401 |
| | | | 604/117 |
| 8,920,388 B2* | 12/2014 | Slocum | A61B 17/3401 |
| | | | 604/272 |
| 9,743,875 B2* | 8/2017 | Maguire | A61M 5/427 |
| 10,646,660 B1* | 5/2020 | Hochman | A61M 5/3129 |
| 2013/0066191 A1* | 3/2013 | Parihar | A61B 5/055 |
| | | | 600/417 |
| 2019/0192247 A1* | 6/2019 | Woo | A61B 34/74 |
| 2020/0397399 A1* | 12/2020 | Adams | A61B 8/5253 |
| 2021/0378627 A1* | 12/2021 | Yarmush | A61B 5/150748 |

FOREIGN PATENT DOCUMENTS

| | | |
|---|---|---|
| CN | 106943180 A | 7/2017 |
| CN | 108567475 A | 9/2018 |
| CN | 108577945 A | 9/2018 |
| CN | 111150462 A | 5/2020 |
| CN | 111166437 A | 5/2020 |
| CN | 211674480 U | 10/2020 |

\* cited by examiner

AUXILLIARY DEVICE AND AUXILLIARY METHOD FOR EPIDURAL ANESTHESIA NEEDLE PLACEMENT

CROSS-REFERENCE TO RELATED APPLICATIONS

This application is a bypass continuation application of PCT application no.: PCT/CN2021/075507. This application claims priorities from PCT Application PCT/CN2021/075507, filed Feb. 5, 2021, Chinese Patent Application No. 202010096955.7, entitled "Auxiliary Method for Epidural Anesthesia Needle Placement"; and to Chinese Patent Application No. 202010096939.8, entitled "Auxiliary Device for Epidural Anesthesia Needle Placement", filed with China Patent Bureau on Feb. 17, 2020, which are incorporated by reference in their entirety into this application.

TECHNICAL FIELD OF THE DISCLOSURE

The disclosure relates to the technical field of medical instruments, in particular relates to an auxiliary device and auxiliary method for epidural anesthesia needle placement.

BACKGROUND OF THE DISCLOSURE

Having been applied to clinical practice for more than 90 years, Epidural Anesthesia has been improved step by step in the course of practices and researches, and therefore become a commonly used method in the current clinical anesthesia. Compared with general anesthesia, epidural anesthesia has a lower incidence in pulmonary embolism, deep venous thrombosis, pneumonia, myocardial infarction, wound infection, and respiratory depression, with small influence on body organs and better economy efficiency. However, the current clinical epidural anesthesia is still performed by blind manual operation, where doctors recognize epidural space in dependence on subjective perception, such that there is uncertainty in the positioning of puncture needle and catheter, which renders poor controllability and frequent complications of anesthesia and therefore limits clinical application of the said method.

In the prior art, the technique of "Blind Manual Operation" refers to a technical means in which an anesthetist identifies reaching to the epidural space by feeling disappearance of epidural resistance via his/her fingers. Since this depends on subjective determination, the rate of success is mainly decided by clinical experiences of the anesthetist. In actual clinical practice, due to lack of consistent assessment standards of epidural anesthesia effect, the failure rate of clinical epidural anesthesia is always underestimated. "Blind Manual Operation" may cause the following issues: incorrect epidural anesthesia needle placement, catheter repositioning after positioning, local overdose of anesthetics, positioning deviation of puncture point, long-time uncomfortable posture of the patient, and etc., all of which may affect the final effect of anesthesia to varying degree and bring uncomfortable experiences to the patient.

Furthermore, as for the technique of "Blind Manual Operation", even the most experienced anesthetist also has a certain rate of failure. Particularly, the operation of epidural anesthesia puncture, catheter placement may become very difficult in the case of elder patients, spinal stenosis, narrowed epidural space, calcification of yellow ligament and etc.

Over the recent decades, in addition to the improvement of anesthesia puncture kit, there is no extraordinary improvement and development in the aspect of technical operation of epidural anesthesia, and so far there is no good solution for an "ideal epidural space positioning technique based on objective indications", so that the defects existing in manual operation become the main technical obstacle of epidural anesthesia.

DISCLOSURE OF THE DISCLOSURE

The present application aims at providing an auxiliary device and method for epidural anesthesia needle placement to solve the difficulty of anesthetists in accurate puncture.

In order to solve the above problem, the present disclosure provides an auxiliary device for epidural anesthesia needle placement, comprising: a needle placement unit, a motion guide unit for driving the needle placement unit into movement, and a control unit for supporting and controlling the motion guide unit, the needle placement unit being electrically connected to the control unit; the needle placement unit comprises: a first support connected to the motion guide unit, a second support connected to the first motion guide unit, a needle placement assembly slidably connected to the second support, and a first drive arranged on the first support for driving the second support into movement.

According to an aspect of the present disclosure, the movement direction of the needle placement assembly on the second support is parallel to the movement direction of the second support on the first support.

According to an aspect of the present disclosure, the first drive drives the second support to linearly reciprocate on the first support.

The needle placement assembly linearly reciprocates on the second support.

According to an aspect of the present disclosure, the needle placement assembly is provided with a pressure sensor.

In the movement direction of the needle placement assembly, a first stop abutting against the pressure sensor is arranged opposite to the second support and a second stop for limiting a movement position of the needle placement assembly.

According to an aspect of the present application, the needle placement assembly further comprises: a third support slidably connected to the second support, a fourth support detachably connected to the third support, and a puncture needle mounted on the fourth support.

According to an aspect of the present application, the space between the first stop and the second stop is L1, and the distance between an end at which the pressure sensor abuts against the first stop and an end at which the third support abuts against the second stop is L2, L1≥L2.

According to an aspect of the present application, a sound detection module is provided on a side where the fourth support is in proximity to the puncture needle.

According to an aspect of the present disclosure, the third support is in clip-connection to the fourth support.

The puncture needle is in clip-connection to the fourth support.

According to an aspect of the present application, the puncture needle comprises a puncturing portion and a needle core portion.

The puncturing portion is a hollow cylinder. The needle core portion is arranged coaxially with the puncturing portion in a detachable manner in the hollow portion of the puncturing portion.

A first structural member is provided on an end of the needle core portion, and an end of the puncturing portion which is adjacent to the first structure member adjoins the sound detection module.

According to an aspect of the present disclosure, an electric conductor for electrically connecting the control unit and the puncturing portion is provided on the fourth support.

The puncturing portion is provided with an insulation layer on its outer surface.

According to an aspect of the present disclosure, the insulation layer is a Teflon coating.

According to an aspect of the present disclosure, the first drive comprises: a power source, and a lead screw pair provided integrally with a main shaft of the power source.

In order to achieve the above purpose of the disclosure, the present disclosure provides an auxiliary method for epidural anesthesia needle placement, comprising:

S1: obtaining a target point of a target region, by means of the control unit, controlling the motion guide unit to direct the needle placement unit to the target point;

S2: driving the needle placement unit in a puncture direction, by means of the control unit, receiving an electric signal fed back from the needle placement unit, and determining whether or not a needle stop signal is triggered in accordance with the electric signal, if yes, stop driving the needle placement unit;

S3: evaluating the puncture result of the needle placement unit and outputting a evaluation result.

According to an aspect of the present disclosure, in step S2, the electric signal is one of a resistance change signal, a needle advance displacement signal, an electrophysiological monitoring signal, and a puncture-tissue differentiation signal.

According to an aspect of the present disclosure, the pressure sensor provided for the needle placement assembly of the needle placement unit is for outputting the resistance change signal, and the first drive of the needle placement unit is for outputting the needle advance displacement signal.

According to an aspect of the present disclosure, the electrophysiological monitoring signal and the puncture tissue differentiation signal are acquired based on a puncture position of the puncturing portion on the puncture needle of the needle placement assembly.

According to an aspect of the present disclosure, in step S2, when the electric signal is the resistance change signal, if a hopping occurs in the resistance change signal, the needle stop signal is triggered to stop driving the needle placement unit.

According to an aspect of the present disclosure, in step S2, when the electric signal is the needle advance displacement signal, an actual displacement of needle advancement is obtained in accordance with the needle advance displacement signal of the first drive, and comparing the actual displacement of needle advancement with a predetermined distance of puncture path, if the actual displacement of needle advancement exceeds the predetermined distance of puncture path, the needle stop signal is triggered to stop driving the needle placement unit.

According to an aspect of the present disclosure, in step S2, when the electric signal is the electrophysiological monitoring signal, the needle stop signal is triggered to stop driving the needle placement unit.

According to an aspect of the present disclosure, in step S2, when the electric signal is the puncture-tissue differentiation signal, a current tissue conductivity contained in the puncture-tissue differentiation signal is matched with a pre-established tissue conductivity data base to determine whether or not the puncture needle is in place, if yes, the needle stop signal is triggered to stop driving the needle placement unit.

According to an aspect, in the step of determining whether or not the puncture needle is in place in accordance with a matching result, the puncture process of the puncture needle is visually stimulated and displayed in accordance with the matching result.

According to an aspect of the present disclosure, in step S3, in the step of evaluating the puncture result of the needle placement unit, evaluation is carried out using an auxiliary determination method of acoustic detection and/or an auxiliary determination method of pressure cavity detection.

According to an aspect of the present disclosure, in the step of evaluating with the auxiliary determination method of acoustic detection, the needle core portion of the puncture needle is pulled out of the puncturing portion. When the sound detection module detects removal of the needle core portion from the puncturing portion, the sound generated as drawing the air into the puncturing portion is converted into an electric signal by the sound detection module and transmitted to the control unit for evaluation.

According to an aspect of the present disclosure, in the step of evaluating with the auxiliary determination method of pressure cavity detection, the evaluation is executed by positively and negatively rotating an injection pump which is in communication with the puncturing portion; a pressure cavity sensor is provided inside the injection pump.

According to an aspect of the present disclosure, the step of positively and negative rotating the injection pump for evaluation comprises: positively rotating the injection pump, acquiring a pressure change of the pressure cavity using the pressure cavity sensor and transmitting it to the control unit for evaluation; negatively rotating the injection pump, performing evaluation in accordance with whether or not there is outflow of fluid.

According to a solution of the present disclosure, the disclosure may sufficiently stimulates the skill of manual puncture, performing a real-time multidimensional monitoring to the puncture process based on "Resistance Disappearance Method", "Negative Pressure Method", human neurophysiological reactions, and other clinical experiences, in combination with intraoperative image positioning technique, multi-sensor technique, electrophysiological monitoring technique, and micromechanical control technique, and consequently achieving an autonomous, precise, and safe needle placement operation.

According to a solution of the present disclosure, by means of multi-sensor technique, the puncture process and the determination following the puncture are scientifically, reliably detected, enormously reducing the possibility of misjudgment. Furthermore, electrophysiological monitoring is also added in the puncture process which eliminates occurrence of a case with a serious consequence, such as total spinal anesthesia, caused by puncture failure.

According to a solution of the present disclosure, it is possible to accurately control a deep of puncture independently of the clinical experience of anesthetists. In the solution, pressure monitoring, electrophysiological monitoring, and electric signal monitoring can be achieved, and stepping control technique can be used to perform real-time monitoring and control over the puncture process. When the puncture needle pierces through yellow ligamentum, reaching epidural space, the needle placement mechanism does not have overshoot and may accurately control the deep of puncture.

According to a solution of the present disclosure, the electrical single monitoring is execute by connecting a conductor to the puncture needle, where the sensor measures an electrical conductivity of the current tissue in real time, and simulates the current tissue in accordance with a data base of electrical conductivity, that is, a real-time puncture position of the puncture needle can be simulated, and at the same time a current needle position of the puncture needle can be calculated in real time by means of the advance path and distance, the pressure data, and the stepping pulse data of the needle placement unit, followed by merging the simulation data, a real position of the puncture needle into skin is accurately calculated and displayed in a system UI interface, and a precise visualization of the puncture process is therefore achieved.

According to a solution of the present disclosure, the disclosure has various monitoring means, where multi-sensor technique is used to scientifically, reliably detect both of the puncture process and the determination following the puncture, enormously reducing the possibility of misjudgment.

DESCRIPTION OF THE PREFERRED EMBODIMENTS

In order to more clearly illustrates embodiments of the present disclosure or technical solutions in the prior art, figures used in the embodiments are simply introduced as follows. Apparently, the figures in the following description are merely some embodiments of the present disclosure. Person skilled in the art could also obtain other figures in accordance with these figures without contributing innovative effort.

As describing embodiments of the present disclosure, the orientations or position relationships represented by terms "longitudinal", "transverse", "upper", "lower", "front", "rear", "left", "right", "vertical", "horizontal", "top", "bottom", "inner", "outer" are orientations or position relationships shown based on the related figures, which are merely for the purpose of describing and simplifying the present disclosure, but do not indicate or imply that the said devices or elements must have certain orientations, and are configured and operated in certain orientations, so that the above terms cannot be understood as limits to the present disclosure.

Hereinafter, the present disclosure is described in detail in combination with figures and specific embodiments that cannot be specified here, however, embodiments of the present disclosure are not limited to the following embodiments.

Figure 1:
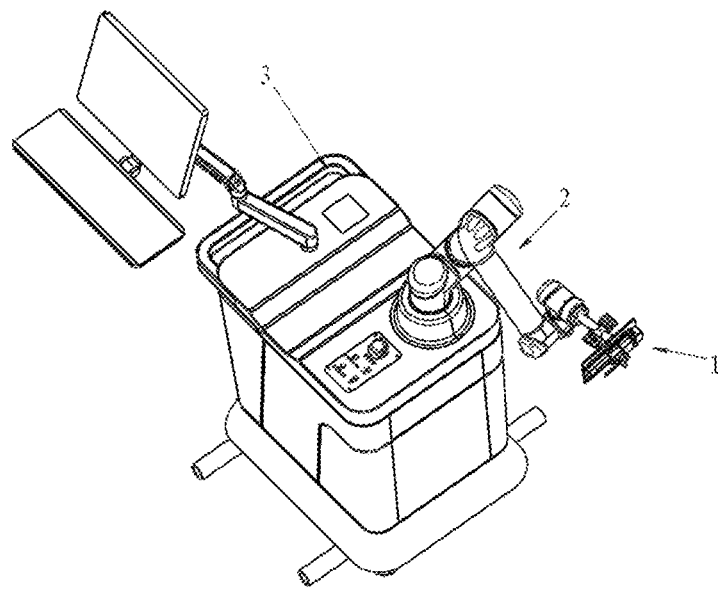
FIG. 1 schematically shows a structure diagram of an auxiliary device in an embodiment according to the present disclosure.
Figure 2:
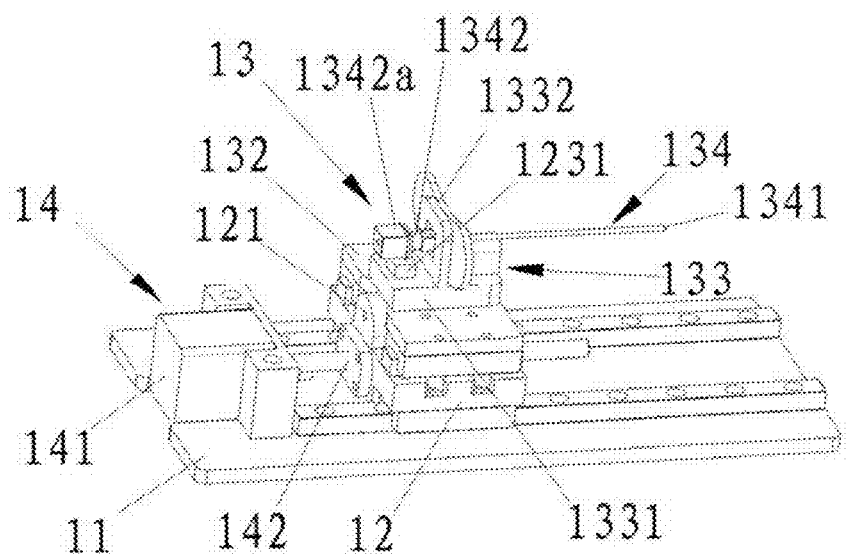
FIG. 2 schematically shows a structure diagram of a needle placement unit in an embodiment according to the present disclosure.
Figure 3:
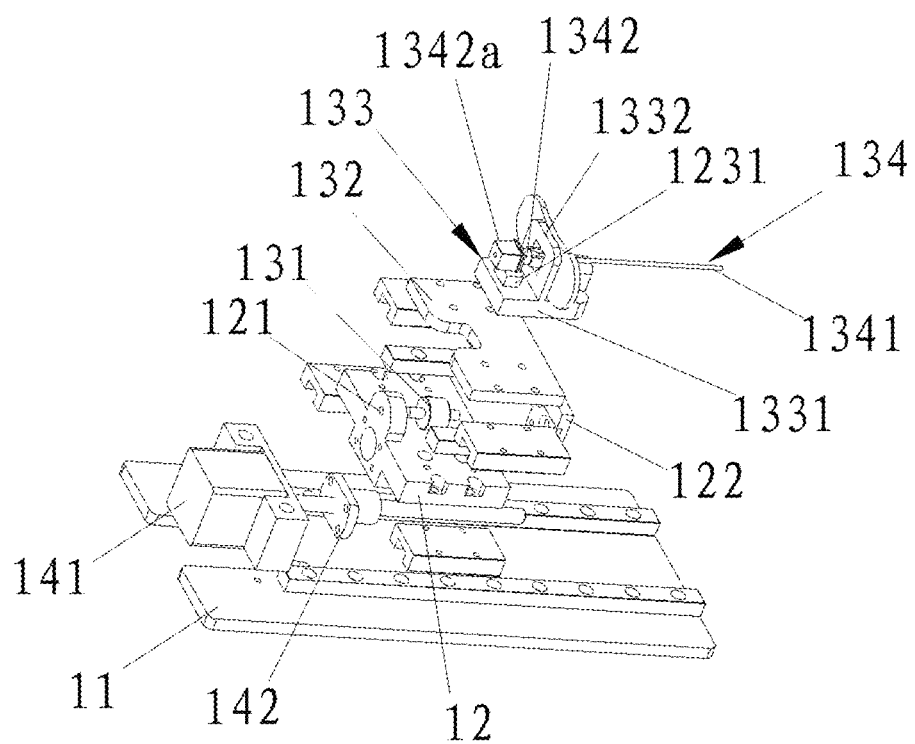
FIG. 3 schematically shows an exploded diagram of a needle placement unit in an embodiment according to the present disclosure.
Figure 4:
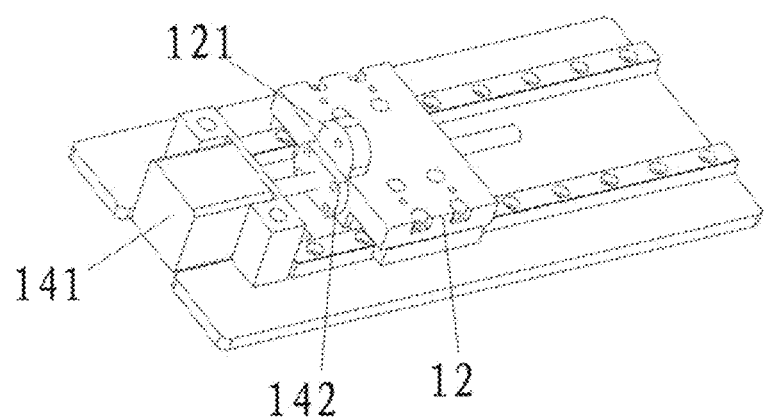
FIG. 4 schematically shows a structure diagram of connection between a first support and a second support in an embodiment according to the present disclosure.
Figure 5:
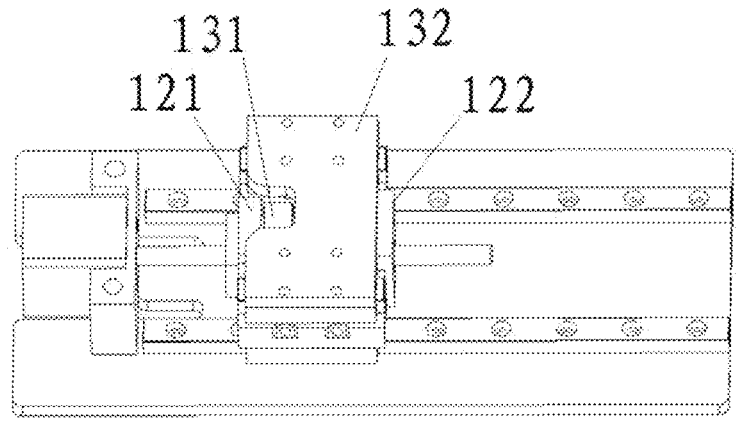
FIG. 5 schematically shows a structure diagram of connection between a third support and a second support in an embodiment according to the present disclosure.
Figure 6:
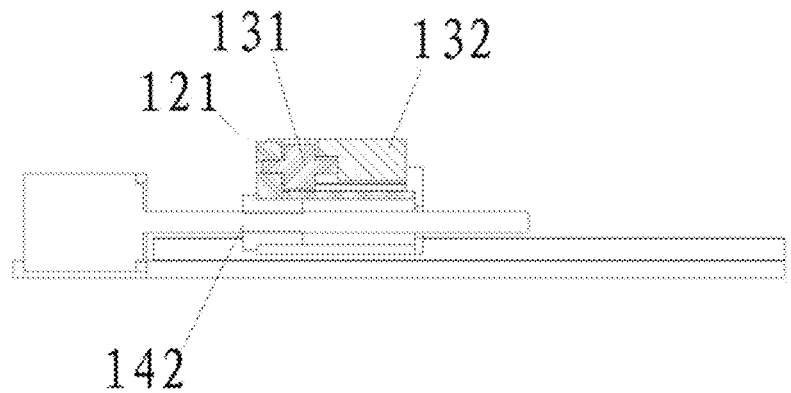
FIG. 6 schematically shows a cross-sectional diagram of a connection structure between a third support and a second support in an embodiment according to the present disclosure.

As shown in combination with FIG. 1, FIG. 2, and FIG. 3, according to an embodiment of the present disclosure, the auxiliary device for epidural anesthesia needle placement of the present disclosure comprises: a needle placement unit 1, a motion guide unit 2 for driving the needle placement unit 1 into movement, and a control unit 3 for supporting and controlling the motion guide unit 2, the needle placement unit 1 being electrically connected to the control unit 3. In the present embodiment, the needle placement unit 1 comprises: a first support 11 connected to the motion guide unit 2, a second support 12 slidably connected with the first support 11, a needle placement assembly 13 slidably connected with the second support 12, and a first drive 14 arranged on the first support 11 for driving the second support 12 into movement. In the present embodiment, the motion guide unit 2 can be controlled via the control unit 3 to drive the needle placement unit 1 to execute a puncture operation, achieving automation of the puncture process.

As shown in combination with FIG. 2 and FIG. 3, according to an embodiment of the present disclosure, the movement direction of the needle placement assembly 13 on the second support 12 is parallel to the movement direction of the second support 12 on the first support 11.

As shown in combination with FIG. 2 and FIG. 3, according to an embodiment of the present disclosure, the first drive 14 drives the second support 12 to linearly reciprocate on the first support. The needle placement assembly 13 reciprocates linearly on the second support 12, while the needle placement assembly 13 and the second support 12 are not driven via any driving element. In the present embodiment, the first drive 14 comprises: a power source 141 and a lead screw pair 142. The first drive 14 can be connected to the lead screw pair via a stepping motor to construct a linear driving device, in which stepping motor the main shaft is arranged integrally with the lead screw pair. Certainly, the first drive 14 may also be developed directly by an integral driving device, such as an electric cylinder and etc. By configuring the main shaft of the stepping motor as a ball screw, in the process of driving the lead screw into rotation via the motor, traditional components, such as a coupling and the like, can be omitted, which effectively reduce the volume and rotational inertia of the first drive, and thereby enhance response speed of the first drive 14.

As shown in combination with FIG. 2, FIG. 3, FIG. 4, FIG. 5 and FIG. 6, according to an embodiment of the present disclosure, the needle placement assembly 13 is provided with a pressure sensor 131. In the present embodiment, in the movement direction of the needle placement assembly 13, a first stop 121 abutting against the pressure sensor 131 and a second stop 122 for limiting a movement positon of the needle placement assembly are disposed opposite to each other on the second support 12. In the present embodiment, when the first drive 14 drives the second support 12 forwards, if the needle placement assembly 13 is subjected to a resistance in the front, the needle placement assembly 13 will move backwards under the action of the resistance, until the pressure sensor 131 abuts against the first stop 121. In this case, the first drive 14 continues to drive the second support 12 forwards, while the pressure sensor 131 converts the received resistance into an electric signal and outputs the same to the control unit 3, so that it is possible to obtain the change of resistance acting on the needle placement assembly 13 during the puncture process via the conversion by control unit 3. When the first drive 14 drives the second support 12 backwards, if the needle placement assembly 13 is subjected to a friction resistance opposing the movement direction, the needle placement assembly 13 moves in a direction towards the second stop 122, until it abuts against the second stop 122, and the first drive 14 continues to drive the second support 12 backwards, under the action of abutting against the second stop 122, it is easy for the needle placement assembly 13 to overcome the resistance acting thereon and to further move backwards along with the first drive 14.

As shown in combination with FIG. 2 and FIG. 3, according to an embodiment of the present disclosure, the needle placement assembly 13 also comprises: a third support 132 for slidably connecting to the second support 12, a fourth support 133 for detachably connecting to the third support 132, and a puncture needle 134 mounted on the fourth support 133. In the present embodiment, the third support 132 is in clip connection to the fourth support 133; the puncture needle 134 is in clip connection to the fourth support 133. By means of the above arrangement, it is easy to achieve quick assembly, disassembly and replacement of the third support 132, the fourth support 133, and the puncture needle 134, and thereby enhancing the efficiency of assembling, disassembly, and replacement. Moreover, the use of clip connection provides a higher precision of positioning, such that it is advantageous for guarantee of the puncture accuracy of the present disclosure.

As shown in combination with FIG. 2 and FIG. 3, according to an embodiment of the present disclosure, the third support 132 is slidably connected to the second support 12 via sliding rails. The fourth support 133 comprises a connection plate 1331 and a bearing plate 1332 which are arranged perpendicularly to each other. In the present embodiment, the connection plate 1331 and the third support 142 are in clip connection, the puncture needle 134 and the bearing plate 1332 are in clip connection. In the present embodiment, the bearing plate 1332 is located on a side of the connection plate 1331, and the puncture needle 134 is located on the same side of the connection plate 1331.

As shown in combination with FIG. 2 and FIG. 3, according to an embodiment of the present disclosure, the fourth support 133 is provided with a sound detection module 1231. In the present embodiment, the sound detection module 1231, the puncture needle 134, and the bearing plate 1332 are located on the same side of the connection plate 1331. In this case, the sound detection module 1231 is directly mounted on a surface of the connection plate 1331, and, in the thickness direction of connection plate 1331, the sound detection module 1231 is spaced apart from the puncture needle 134.

As shown in combination with FIG. 2 and FIG. 3, according to an embodiment of the present disclosure, the puncture needle 134 comprises a puncture portion 1341 and a needle core portion 1342. In the present embodiment, the puncture portion 1341 is a hollow cylinder, and the needle core portion 1342 is arranged coaxially with the puncture portion 1341 in a detachable manner in the hollow space of the puncture portion 1341. The needle core portion 1342 is a solid cylinder. By inserting the needle core portion 1342 into the puncture portion 1341, the hollow space of puncture portion 1341 is blocked, such that the puncture portion 1341 of puncture needle 134 is not in communication with the external environment during the puncture process. When there is a need to detach the core portion 1342, it is only required to clamp an end of the core portion 1342 and pull it out of the puncture portion 1341.

As shown in combination with FIG. 2 and FIG. 3, in the present embodiment, an end of the core portion 1342 is provided with a first structural member 1342*a*, the end of the puncture portion 1341 which is adjacent to the first structural member 1342*a* being adjacent to the sound detection module 1231. In the present embodiment, by disposing the first structural member 1342*a* on the needle core portion 1342, it is possible to conveniently pull out the needle core portion 1342 inserted in the puncture portion 1341. Furthermore, by abutting the first structural member 1342*a* against the puncture portion 1341, it is possible to efficiently enhance seal effect between the core portion 1342 and the hollow space of puncture portion 1341, thereby ensuring use property of the present disclosure.

Figure 11:
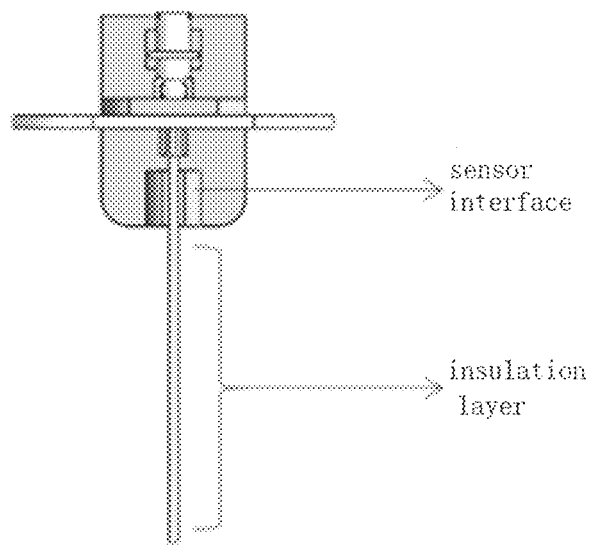
FIG. 11 schematically shows a structure diagram of a puncture needle of a puncture process in an embodiment according to the present disclosure.

As shown in combination with FIG. 2 and FIG. 3, according to an embodiment of the present disclosure, the fourth support 133 is provided with an electric conductor for electrically connecting the control unit 3 to the puncture portion 1341; the puncture portion 1341 is provided with an insulation layer on its outer surface (see FIG. 11). In the present embodiment, the insulation layer 1341 is a Teflon coating. In the present embodiment, the puncture portion 1341 is made of a metal material, such that providing an insulation layer on its outer surface may effectively achieve the effect of making the puncture portion 1341 electrically conductive in the needle tip, but insulated in other parts. Moreover, the use of a Teflon coating also has lubrication effect which endows the present disclosure with a better puncture effect. In the present embodiment, electrophysiological monitoring of the puncture position is achieved by providing, on the fourth support 133, an electrical conductor which electrically connects the control unit 3 and the puncture portion 1341 (see FIG. 11). Specifically, when the puncture portion 1341 touches a nerve root, the electric signal on the needle tip may stimulates the nerve, in which case the control unit 3 may make a corresponding response and control the puncture portion 1341 to stop moving, guaranteeing safety, accuracy and stability of the puncture process.

According to an embodiment of the present disclosure, if the space between the first stop 121 and the second stop 122 is L1, the distance between the end of pressure sensor 131 which abuts against the first stop 121 and the end of third stop 132 which abuts against the second stop is L2, L1≥L2. In the present embodiment, if the space between the first stop 121 and the second stop 122 is L1, the distance between the end of pressure sensor 131 which abuts against the first stop 121 and the end of third support 132 which abuts against the second stop 122 is L2, and the difference between L1 and L2 is less than or equal to 0.05 mm, L1-L2≤0.05 mm. In the present embodiment, in the case of high machining precision between components, a smaller difference between L1 and L2 is better, which may guarantee accuracy and precision of the puncture process.

According to an embodiment of the present disclosure, the motion guide unit 2 is a laser guide system having a function of surgery planning. In the present embodiment, the needle placement unit 1 carries out the puncture operation along a predefined path under the action of motion guide unit 2.

According to the present disclosure, by disposing a sound detection module on the fourth support, when the puncture needle enters in an object, followed by pulling out the core portion, the sound detection module may, due to the negative pressure produced between the external environment and the hollow space in the puncture portion, effectively and quickly detect the moment at which the needle core portion is pulled out of the puncture portion. Depending on the detected sound, the present disclosure may more quickly and accurately detect the quality of puncture, such that the device of the present disclosure may conveniently, effectively and multi-dimensionally evaluate the puncture result.

According to the present disclosure, by way of electrifying the puncture needle and providing an insulation layer on the outer surface of the puncture needle, the needle tip of the puncture needle becomes electrically conductive, and a corresponding puncture position is further obtained depending on the electric signal of the needle tip. In the case that a puncture operation is executed by the needle placement unit of the present disclosure, if the puncture needle touches a nerve root, the electric signal will stimulate the nerve, and the control unit will further acquire a corresponding electric signal, giving a sound signal, and at the same time triggering a protection mechanism and stopping the movement of the mechanism. Hence, the solution of the present disclosure further effectively enhances puncture precision of the present disclosure.

Figure 7:
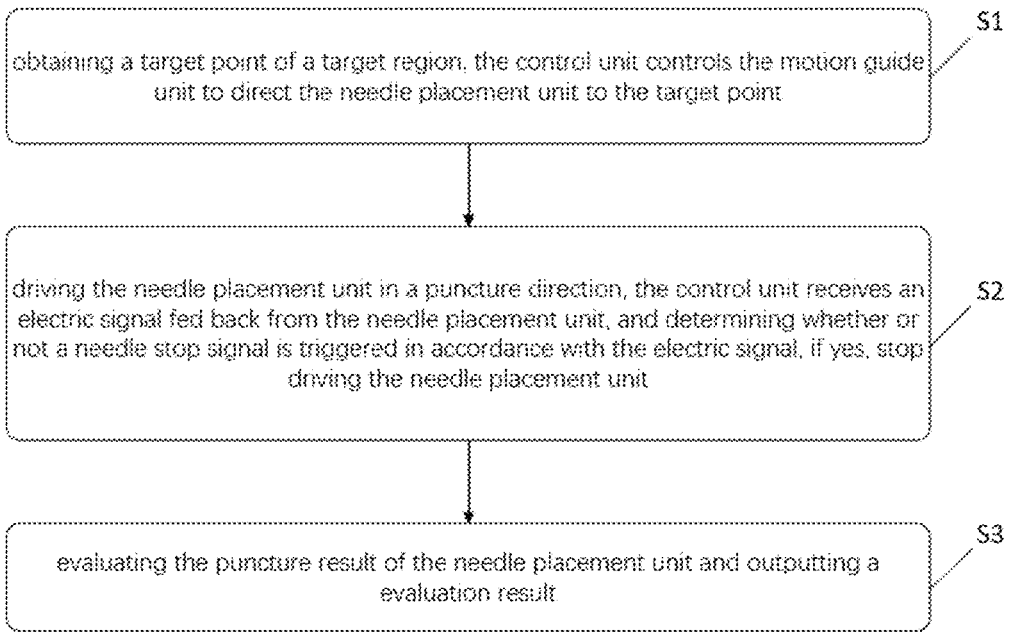
FIG. 7 schematically shows a step block diagram of an auxiliary method in an embodiment according to the present disclosure.
Figure 8:
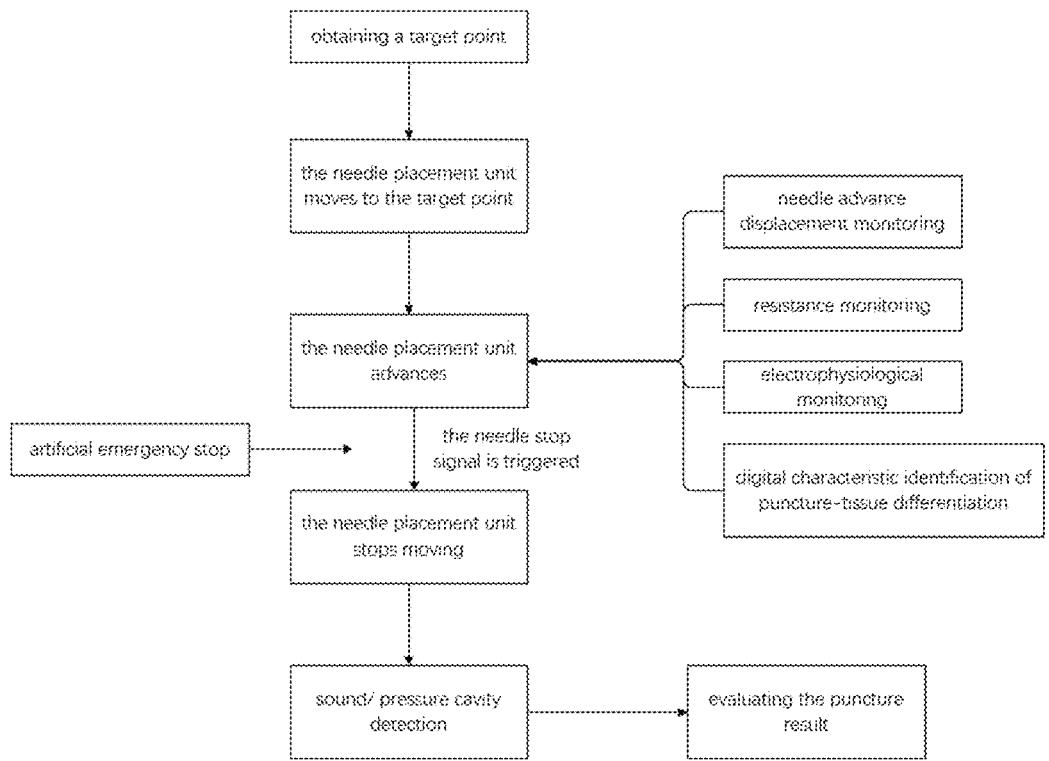
FIG. 8 schematically shows a flow chart of an auxiliary method in an embodiment according to the present disclosure.

As shown in combination with FIG. 7 and FIG. 8, according to an embodiment of the present disclosure, an auxiliary method for epidural anesthesia needle placement of the present disclosure is applied to the above mentioned auxiliary device, the auxiliary method comprising:

S1: obtaining a target point of a target region, controlling, by means of the control unit 3, the motion guide unit 2 to direct the needle placement unit 1 to the target point;

S2: driving the needle placement unit 1 in a puncture direction, receiving, by means of the control unit 3, an electric signal fed back from the needle placement unit, and determining whether a needle stopping signal is triggered depending on the electric signal, if yes, stop driving the needle placement unit 1;

S3: evaluating the puncture result of the needle placement unit 1 and outputting an evaluation result.

Figure 9:
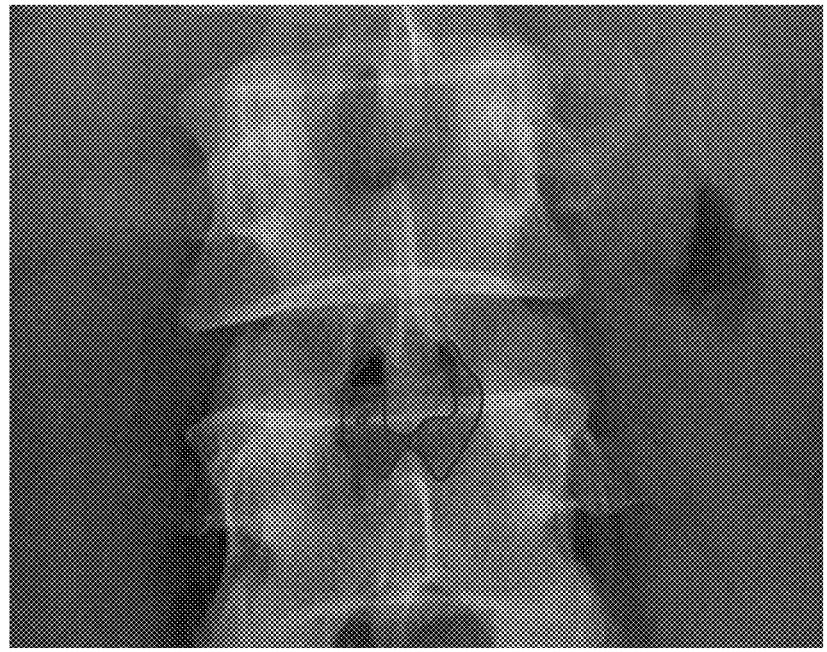
FIG. 9 schematically shows a position diagram of a target region and a target point in an embodiment according to the present disclosure.

As shown in combination with FIG. 1 and FIG. 7, according to an embodiment of the present disclosure, in step S1, a target point of the target region is obtained, and in the step of the control unit 3 controlling the motion guide unit 2 to direct the needle placement unit 1 to the target point, the device for epidural anesthesia needle placement of the present disclosure is calibrated in advance mainly by way of performing an image positioning via the motion guide unit 2. Having finished calibration of the device, an X-ray film of the target position which requires a surgery is obtained by means of a C-arm X-ray machine, the target region (see the closed-loop region in FIG. 9) is obtained by intraoperative image positioning, and further the target point in the target region is selected (see the point in the closed-loop region in FIG. 9). Having chosen the target point, the control unit 3 drives the motion guide unit 2 into movement depending on the selected target point, further guiding the motion guide unit 2 to direct the pose of the needle placement unit connected thereto to the target point in order to subsequently execute a puncture operation.

As shown in combination with FIG. 1, FIG. 7 and FIG. 8, according to an embodiment of the present disclosure, in the step S2, the operator starts needle placement operation after having confirmed that the needle placement unit 1 is moved to the target position, that is, the motion guide unit 2 drives the puncture needle 134 on the needle placement unit 1 in a puncture direction, while the system carries out a multi-dimensional monitoring, such as a real-time resistance monitoring, a needle displacement monitoring, an electrophysiological monitoring, and a digital characteristic identification of the differentiation of punctured tissues, to the needle placement process, when any of which monitoring means triggers a needle stopping signal, the needle placement mechanism shall stop moving immediately and provide prompt information.

As shown in combination with FIG. 1, FIG. 7 and FIG. 8, according to an embodiment of the present disclosure, in the step S2 in which the control unit 3 receives an electric signal fed back from the needle placement unit 1, the electric signal is at least one of a resistance change signal, a needle displacement signal, an electrophysiological signal, a puncture tissue differentiation signal. As the above mentioned, in the present embodiment, the resistance change signal is acquired via the pressure sensor 131, the needle displacement signal is acquired via the first drive 14, and the electrophysiological signal and the puncture tissue differentiation signal are acquired via the puncture needle.

Figure 10:
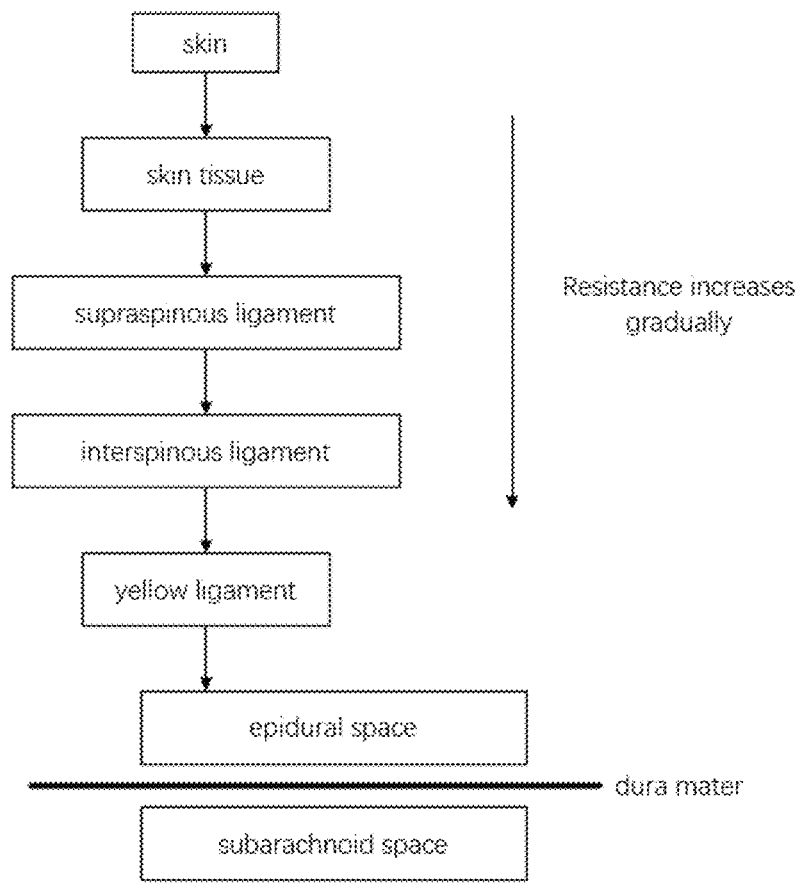
FIG. 10 schematically shows a diagram of resistance change of a puncture process in an embodiment according to the present disclosure.

In the present embodiment, a resistance change signal is adopted during the resistance monitoring. Referring to FIG. 10, the resistance monitoring is specifically based on "Loss of Resistance" which is commonly used in clinical practice, that is, when the puncture needle pierces through skin, skin tissue, supraspinous ligament, and interspinous ligament in sequence, the resistance of puncture increases gradually and reaches a maximum as arriving at yellow ligament (it can be understood as the fact that when pushing the syringe, air is compressed, man therefore has a sensation of resistance). At the right moment when the puncture needle penetrates the yellow ligament, the resistance against advancement suddenly disappears (it can be understood as the fact that when pushing the syringe, resistance disappears and air is not compressed, man therefore has a sensation of loss, while no encephalon is taken out along with the withdrawal). Here, the resistance against needle advancement of the puncture needle shall have a hopping process. Hence, in the puncture process, the pressure sensor 1 disposed in the needle placement unit 1 of the present disclosure may also output a pressure change process which is similar to or as same as the above mentioned, i.e., the pressure increases gradually until a decrease occurs in a hopping manner. It is known from the above process that the pressure sensor 131 may monitor the resistance against the puncture needle 134 in real time during the puncture process. As passing through yellow ligament, the resistance detected may have an obvious hopping (it shall be noted that this hopping is a relative change, not an absolute value). Further, in the step S2, when the electric signal is a resistance change signal, a needle stopping signal is triggered to stop driving the needle placement unit 1, if the resistance change signal has a hopping.

In the present embodiment, a needle displacement signal is used in the needle displacement monitoring. Specifically, during the needle displacement monitoring, when the puncture needle enters skin, the pulse number of the stepping motor is recorded by means of a counter provided in the device so as to obtain the needle displacement signal in real time after piercing the puncture needle into skin. Further, in the step S2, when the electrical signal is a needle displacement signal, as the above stated, by way of acquiring CT data of the preoperative puncture site of the patient in advance, a planned route distance in the puncture operation may be obtained depending on the CT data, such that by comparing the planned route distance with an actual displacement, the system can provide prompt information and triggers a stop signal, when the actual displacement exceeds the planned route distance. In the embodiment, the entrance of puncture needle into the skin is determined depending on the change of pressure detected by the pressure sensor.

In the present embodiment, the electrophysiological monitoring uses an electrophysiological monitoring signal. Specifically, the intraoperative electro-neurophysiological monitoring is for monitoring the integrity of a function of nervous system in dangerous state during the surgery using various electro-neurophysiological techniques. Hence, it is an indispensable component for improvement of surgery quality to apply electrophysiological monitoring in clinical operations to monitor the integrity of nerve function, reducing nerve damage.

In modern surgical operations, various imaging techniques enormously contribute to the development of operative surgery in the aspect of anatomical structure. Result of the intraoperative electro-neurophysiological monitoring is to find out whether or not a nerve system is damaged in function, so as to objectively evaluate the integrity of nerve system function of a patient in neurosurgical, orthopedic, cardiac-surgical, and facial operations and etc., in order to provide reliable information for surgeons which may in turn perform the operation more smoothly and safely.

Hence, the present disclosure adopts myoelectric nerve monitoring technique in electro-neurophysiological monitoring techniques to know whether the puncture needle placed in human body is too close to spinal nerves via a stimulation electromyogram produced by stimulating nerve rootlets. The myoelectric nerve monitoring technique is applied in the present disclosure in such a way that the structure of the puncture needle is modified in the manner of combining the whole of the current myoelectric nerve monitoring system and anesthesia puncture. Referring to FIG. 10, in an embodiment of the present disclosure, a rod portion of the puncture needle is coated with an insulating layer (such as a Teflon coating), while its tip is electrically conductive. Meanwhile, an electrical conductor which is connected to an interface of the sensor via a wire is provided at the connection between the puncture needle and the fourth support 133. By way of performing a partial insulation treatment thereon and connecting a corresponding sensor thereto, the puncture needle is thereby modified as a probe which is capable of being used for myoelectric nerve monitoring equipment. When the motion guide unit 2 controls the puncture needle to carry out a puncture operation, if the puncture needle touches a nerve root, the needle tip will stimulates the nerve via an electric signal, while the sensor connected thereto may receive a corresponding electric signal, and the control unit 3 converses the corresponding electric signal and generates a sound signal, triggering the protection mechanism at the same time to stop moving the needle placement unit 1.

In the present embodiment, the digital characteristic identification of puncture tissue differentiation uses a puncture tissue differentiation signal. Specifically, electrical conductivities under different tissues can be acquired in combination with the above mentioned electric signals fed back from the muscular electrical stimulation during neuro-electrophysiological monitoring. By establishing a data base of electrical conductivities of different issues in advance, the current position of the puncture needle can be further obtained by comparing the acquired electrical conductivity with the data base. Furthermore, a comparison result can be visually simulated and output on the display device, achieving visualization of the entire puncture process. In the present embodiment, whether the puncture needle 134 is in place according to the comparison result, if so, a needle stop signal is triggered to stop driving the needle placement unit 1.

According to an embodiment of the present disclosure, in step S3, a determination is made by using an assistant determination method of acoustic detection and/or an assistant determination method of pressure cavity detection, in the step of determining a puncture result of the needle placement unit 1.

In the present embodiment, the assistant determination method of acoustic detection is performed by means of a sound detection module 1231. In the embodiment, the assistant determination of acoustic detection is based on the principle of negative epidural pressure commonly used in clinic practice. When the puncture needle penetrates yellow ligament and reaches epidural space, the air outside the needle will be drawn into the negative pressure cavity at the moment the needle core is withdrawn. At this moment, there is an obvious "whoosh" which can be clearly heard with a recurrence rate of substantially 100% in clinic practice. Based on such a clinical phenomenon, the present solution adopts acoustic detection to carry out an assistant determination. In the present disclosure, a detection port of the sensor is encapsulated, which is in a position adjacent to the location at which the core portion 1342 and the puncture portion 1341 of the puncture needle are connected and which is aligned to an air inlet on the puncture needle tail (i.e., the puncture portion 1341 is opposite to a first member 1342a of the core portion 1342), in order to clearly and promptly acquire the sound produced in the withdrawal of the core portion 1342. When a target signal is generated, the sound detection module 1231 may detect a relative change of the acoustic signal, i.e., a result of air being sucked back into the negative pressure cavity is obtained, for the assistant determination of the puncture result.

In the present embodiment, an injection pump is in communication with the puncture portion 1341 and is positively and negatively rotated to perform determination, in the step of performing a determination using the assistant determination method of pressure cavity detection. In the present embodiment, the injection pump is provided with a pressure cavity sensor therein. Specifically, the assistant determination of pressure cavity detection is depending on the "Bubble Method" commonly used in the clinic practice, i.e., if an injector is connected to the tail of the puncture needle, as pushing the injector, man may feel an obvious sensation of resistance, before the puncture needle pierces yellow ligament, and bubbles in the injector are compressed at the same time. After the puncture needle pierces yellow ligament, as pushing the injector, man may feel the resistance disappears, with the bubbles are not compressed and advanced in the direction of saline solution. Based on the above clinic phenomenon, in the present solution, the injection pump is connected for assistant determination of pressure cavity detection, only after withdrawing the needle core and obtaining the result of the assistant determination of acoustic detection.

In the present embodiment, the injection pump is a micro injection pump which is integrated with a pressure cavity sensor for detecting a liquid pressure. The principle of assistant determination of pressure cavity detection is that if the puncture needle does not pierce through yellow ligament, the injection pump rotates positively, the sensor will detect a rapid rise of liquid pressure, while the operator may feel an obvious sensation of resistance in needle advance, just like the feeling when bubbles are compressed in the "Bubble Method". If the puncture needle has pierced through the yellow ligament, the liquid pressure detected by the senor remains substantially unchanged, at which moment the suction direction of the injection pump reverses and no cerebrospinal fluid flows out.

According to the disclosure, by way of performing a real-time, multi-dimensional monitoring to the puncture process of the needle placement unit, for example, monitoring the puncture resistance against the puncture needle in real time by means of the pressure sensor, a puncture depth is recorded once the skin has been pierced through; whether a nerve tissue is touched is monitored in real time by means of the electro-neurophysiological monitoring technique; a conductivity of the current tissue is detected in real time via an electric-signal detection sensor and the current puncture tissue is stimulated according to the conductivity data base. Based on the data detected by multiple sensors, it is determined whether the current position is the target position, ensuring precision of the puncture position during the puncture process, and further enhancing safety during the surgical operation.

According to the disclosure, having finished the puncture, i.e., when it is detected by means of the multiple sensors that the needle placement unit reaches the target position, the present disclosure also provides at least one determination means to assist the determination of puncture result, i.e., uses a sound detection module to detect the back-suction sound of air at the moment when the core portion is withdrawn. Further, an injection pump device with pressure cavity detection is provided for detecting whether the puncture needle is currently in the target position. By the aid of the above detection means, the accuracy of puncture position is further precisely determined.

According to the disclosure, visualization of the puncture process is achieved by detecting the conductivity of the current tissue by means of the electric signal detection sensor and stimulating the current puncture tissue according to the preset tissue conductivity data base, i.e., stimulating the real-time puncture position of the puncture needle and simultaneously calculating an advance path and distance of the puncture needle in the skin in real time by means of a surgery planning function of the apparatus in the present disclosure, calculating the current puncture position in real time via pressure data and stepping pulse data, then, by means of merging with stimulation data, accurately calculating the real position of the puncture needle piercing through the skin, and displaying the real position in the system UI interface so as to achieve precise visualization of the puncture process.

According to the disclosure, the needle placement unit in a form of a double-track arrangement bears, by the aid of the tracks, the bending moment produced by puncture force, preventing thereby the effect of bending moment and ensuring measurement precision and service life of the sensors.

The above content merely concerns examples of the embodiments of the present disclosure. The apparatuses and structures which are not described with details therein shall be understood to be implemented by means of the existing universal apparatuses and methods in the present field.

The above mentioned is only a scheme of the present disclosure and is not intended to limit the present disclosure. For a person skilled in the art, the present disclosure may have various modifications and variations. Any other modifications, equivalent substitutions, adaptations, and etc. made under the spirit and within the concept of the present disclosure shall be encompassed in the protection extent of the present disclosure.

The invention claimed is:

1. An auxiliary device for epidural anesthesia needle placement, comprising: a needle placement unit (1), a motion guide unit (2) for driving the needle placement unit (1) into movement, and a control unit (3) for bearing and controlling the motion guide unit (2), the needle placement unit being electrically connected to the control unit (3);
the needle placement unit (1) comprises: a first support (11) for connecting to the motion guide unit (3), a second support (12) slidably connected with the first support (11), a needle placement assembly (13) slidably connected with the second support (12), and a first drive (14) arranged on the first support (11) for driving the second support (12) into movement.

2. The auxiliary device according to claim 1,
wherein the movement direction of the needle placement assembly (13) on the second support (12) is parallel to the movement direction of the second support (12) on the first support (11).

3. The auxiliary device according to claim 1, wherein the first drive (14) drives the second support (12) to linearly reciprocate on the first support (11); the needle placement unit (13) reciprocates linearly on the second support (12).

4. The auxiliary device according to claim 1, wherein the needle placement assembly (13) is provided with a pressure sensor (131); in the movement direction of the needle placement assembly (13), a first stop (121) able to abut against the pressure sensor (131) and a second stop (122) for limiting a movement position of the needle placement assembly (13) are correspondingly disposed on second support (12).

5. The auxiliary device according to claim 4, wherein the needle placement assembly (13) also comprises: a third support (132) for slidably connecting the second support (12), a fourth support (133) for detachably connecting the third support (132), and a puncture needle (134) mounted on the fourth support (133).

6. The auxiliary device according to claim 5, wherein the space between the first stop (121) the second stop (122) is L1, the distance between an end of the pressure sensor (131) which abuts against the first stop (121) and an end of the third support (132) which abuts against the second stop (122) is L2, then L1≥L2.

7. The auxiliary device according to claim 5, wherein the fourth support (133) is provided with a sound detection module (1231) on a side in proximity to the puncture needle (134).

8. The auxiliary device according to claim 7, wherein the third support (132) is in clip-connection to the fourth support (133); the puncture needle (134) is in clip-connection to the fourth support (133).

9. The auxiliary device according to claim 8, wherein the puncture needle (134) comprises a puncture portion (1341) and a core portion (1342);

the puncture portion (1341) is a hollow cylinder, the core potion (1342) being arranged coaxially with the puncture portion (1341) in a detachable manner in the hollow space of the puncture portion (1341);

an end of the core portion (1342) is provided with a first structural member (1242*a*), an end of the puncture portion (1341) which is adjacent to the first structural member (1242*a*) adjoining the sound detection module (1231).

10. The auxiliary device according to claim 9, wherein the fourth support (133) is provided with an electric conductor for electrically connecting the control unit (3) and the puncture portion (1341); the puncture portion (1341) is provided with an insulating layer on its outer surface.

11. The auxiliary device according to claim 10, wherein the insulating layer is a Teflon coating.

12. The auxiliary device according to claim 1, wherein the first drive (14) comprises: a power source (141) and a lead screw pair (142) arranged integrally with a main shaft of the power source (141).

\* \* \* \* \*